(12) United States Patent
Gorsuch et al.

(10) Patent No.: US 7,195,711 B2
(45) Date of Patent: Mar. 27, 2007

(54) SPECIALIZED HOLLOW FIBER MEMBRANES FOR IN-VIVO PLASMAPHERESIS AND ULTRAFILTRATION

(75) Inventors: Reynolds G. Gorsuch, Yountville, CA (US); Henry Grage, Alpharetta, GA (US); Harold Handley, Jr., Encinitas, CA (US); Harold Peters, Martinez, CA (US); Jacob C. Kearns, Martinez, CA (US)

(73) Assignee: Transvivo Inc., Napa, CA (US)

( * ) Notice: Subject to any disclaimer, the term of this patent is extended or adjusted under 35 U.S.C. 154(b) by 66 days.

(21) Appl. No.: 10/959,918

(22) Filed: Oct. 6, 2004

(65) Prior Publication Data

US 2005/0121384 A1    Jun. 9, 2005

Related U.S. Application Data

(60) Continuation-in-part of application No. 10/666,185, filed on Sep. 17, 2003, now Pat. No. 6,802,971, which is a division of application No. 09/549,131, filed on Apr. 13, 2000, now Pat. No. 6,802,820.

(51) Int. Cl.
*B01D 69/08* (2006.01)
*B01D 71/68* (2006.01)
*B01D 63/02* (2006.01)

(52) U.S. Cl. .................... 210/500.23; 210/500.41; 604/6.04; 604/6.09; 604/27

(58) Field of Classification Search ............... 210/483, 210/490, 500.23, 500.24, 500.41; 604/4.01, 604/5.01, 6.04, 6.09, 27
See application file for complete search history.

(56) References Cited

U.S. PATENT DOCUMENTS

| 4,832,034 | A | 5/1989 | Pizziconi et al. |
| 4,882,223 | A | 11/1989 | Aptel et al. |
| 4,935,141 | A | 6/1990 | Buck et al. |
| 4,950,224 | A | 8/1990 | Gorsuch et al. |
| 5,145,583 | A | 9/1992 | Angleraud et al. |
| 5,151,082 | A | 9/1992 | Gorsuch et al. |
| 5,152,743 | A | 10/1992 | Gorsuch et al. |
| 5,224,926 | A | 7/1993 | Gorsuch et al. |
| 5,605,627 | A | 2/1997 | Carlsen et al. |
| 5,735,809 | A | 4/1998 | Gorsuch et al. |
| 5,980,478 | A | 11/1999 | Gorsuch et al. |

FOREIGN PATENT DOCUMENTS

| EP | 0 801 973 A1 | 10/1997 |
| EP | 0 882 494 A1 | 12/1998 |
| FR | 2566003 | 12/1995 |
| JP | 9323031 | 12/1997 |

*Primary Examiner*—John Kim
(74) *Attorney, Agent, or Firm*—Knobbe Martens Olson & Bear LLP

(57) ABSTRACT

An in-vivo plasmapheresis and/or in-vivo ultrafiltration membrane comprises elongated hollow fibers each fiber having an interior lumen extending along the fiber length, the fiber wall having a plurality of zones between the inner and outer wall surfaces, each of the zones having a mass density different than the mass density of an adjacent zone. The fiber wall is characterized by having a lower mass density zone at the inner wall surface and a higher mass density zone at the outer wall surface. The fiber is further characterized by having an average elongation breaking force strength of at least about 0.2 lbs. and an average elongation of at least about 45%.

30 Claims, 7 Drawing Sheets

SEM OF SECTION ZONE 1 PORE STRUCTURE

SEM OF FIBER CROSSECTION SECTION ZONES 1, 2 AND 3

SEM OF CROSSECTIONS ZONES 3 AND 4

SPECIALIZED HOLLOW FIBER MEMBRANES FOR IN-VIVO PLASMAPHERESIS AND ULTRAFILTRATION

RELATED APPLICATIONS

This application is a continuation-in-part of U.S. application Ser. No. 10/666,185, filed Sep. 17, 2003, U.S. Pat. No. 6,802,971, which is incorporated herein by reference in its entirety, and which is a divisional of U.S. application Ser. No. 09/549,131, filed Apr. 13, 2000, U.S. Pat. No. 6,802,820.

BACKGROUND OF THE INVENTION

In U.S. Pat. Nos. 4,950,224, 5,152,743, 5,151,082, 5,735,809, and 5,980,478 there are disclosed methods and apparatus for carrying out in-vivo plasmapheresis for separating plasma from other blood components within the body and blood vessels of the patient. The apparatus includes pumping means to create a trans-membrane pressure (TMP) and motivate the flow of fluid from within the in-vivo system, whereby blood plasma is pumped from the patient to a treatment means such as a dialyzer apparatus in which toxic metabolic waste in the plasma is removed. After the plasma is treated for removal of waste products, excess fluids, toxins, and/or other deleterious plasma proteins, the treated plasma is returned and reintroduced to the patients' blood stream. Such methods are referred to as plasma dialysis, ultrafiltration or blood purification. The aforesaid patents are incorporated herein by reference in their entirety.

These methods of toxin removal from blood as taught by the above patents are unique and substantially superior from conventional means of hemodialysis as presently practiced for both acute and chronic kidney failure, primarily because removal of whole blood from the patient's vasculature is eliminated from the procedure using plasma, or portions of the plasma instead. In conventional hemodialysis procedures hollow fiber membranes are used in the ex-vivo dialysis and hemofilter cartridges for blood purification. The blood is routed from the body through the center lumen of the hollow fibers in the cartridges and dialysate fluid is routed over the outside walls of the fibers within the cartridge cavity in counter-flow direction to blood flow. Thus, toxin diffusion and ultrafiltration are from inside the fiber lumen to a compartment outside the fiber walls where the ultrafiltrate and toxin-saturated dialysate are collected for further processing and/or disposal.

Conventional hollow fiber membranes commercially used for present hemodialysis, hemo-ultrafiltration, and dialyzer cartridges fabricated from proprietary and non-proprietary polymer compositions generally utilize two types of morphologies: symmetrical and asymmetrical. In a symmetrical composition, the basic morphology or cellular structure and porosity of the fiber wall is uniform from the inner lumen to the outside surface. In asymmetrical compositions, both morphology and pore structures vary from the inner lumen to the outer surface to meet the high pressure requirements of the filter cartridges in which the TMP inside the fiber lumen is high (100–300 mmHg) while the blood flow itself in the fibers is near stagnant (2–300 ml/min/7,000 fibers=0.042 ml/m/fiber). Commercially available membranes, while acceptable in an encapsulated device external to the body in which the fibers are protected and not subjected to flow and pressure fluctuation, would not be acceptable for an in-vivo placement for safety reasons. Such conventional fiber membranes generally have poor elongation and breaking strength and are not suitable for the demanding environment of the in-vivo, high blood flow (vena cava=2.5 l/min), low TMP ($\leq$50 mmHg), and unencapsulated environment of plasma extraction devices described by the aforesaid patent applications.

SUMMARY OF THE INVENTION

The specialized hollow fiber membranes described herein are capable of separation of plasma and/or plasma components from blood and have the unique morphology, performance properties and materials biocompatible characteristics necessary for effective and optimal utilization for in-vivo vascular implantation as the operating element in devices as described in the aforesaid patents for the separation and extraction of plasma and plasma components from the blood. The hollow fiber membrane is tubular in shape and generally circular in cross-section, having a coaxial inner lumen along the length of the fiber in its center. The wall volume of the fibers is asymmetrical with a variable morphology from the outer diameter to that of the inner diameter, having a higher mass density and smaller mean pore diameter at the outer wall and a lower mass density and larger mean pore diameter at the inner wall. The preferred fibers described herein are characterized by having an average elongation breaking force strength of at least about 0.2 lbs. and preferably above about 0.3 lbs. and an average elongation of at least about 45%, preferably above about 60% and more preferably above about 65%. The walls of preferred fibers are also characterized by a continuum of void bounded by solid frames, a continuous change in mass density from the outer wall surface to the inner wall surface, and substantially without macrovoids. The fibers are designed to facilitate in-vivo plasmapheresis and ultrafiltration by exposing the outside of the fiber to whole blood within a patient's blood vessel and separating plasma and/or plasma components from the blood through the fiber wall from the outside in. The separated plasma or ultrafiltrate (exudate) may be transported ex-vivo via a catheter lumen where it is discarded, or treated by cascade filtration means, dialysis (solute diffusion) means, or other methods known to the art, and returned to the patient via a separate lumen in the catheter. The inner lumen of all fibers in a fiber extraction assembly are in direct fluid communication with the access lumen of the catheter which provides means for transporting the exudate ex-vivo.

DETAILED DESCRIPTION OF THE PREFERRED EMBODIMENTS

Figure 5:
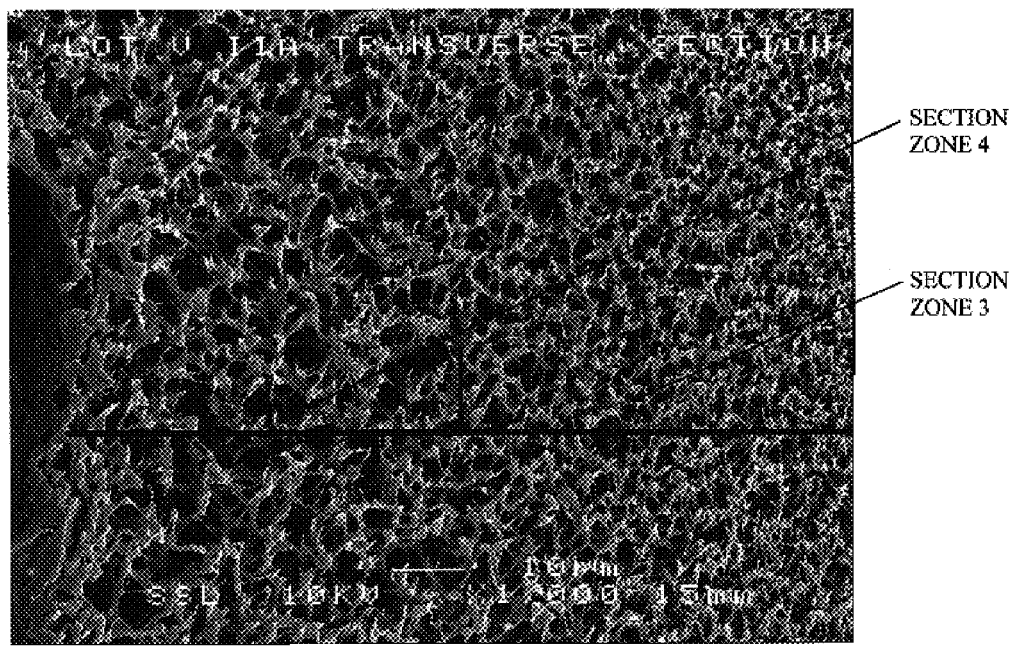
FIG. 5 is a SEM cross-section of Zones 3 and 4 of the fiber shown in FIG. 2 at a magnification of 1,000×.
Figure 6:
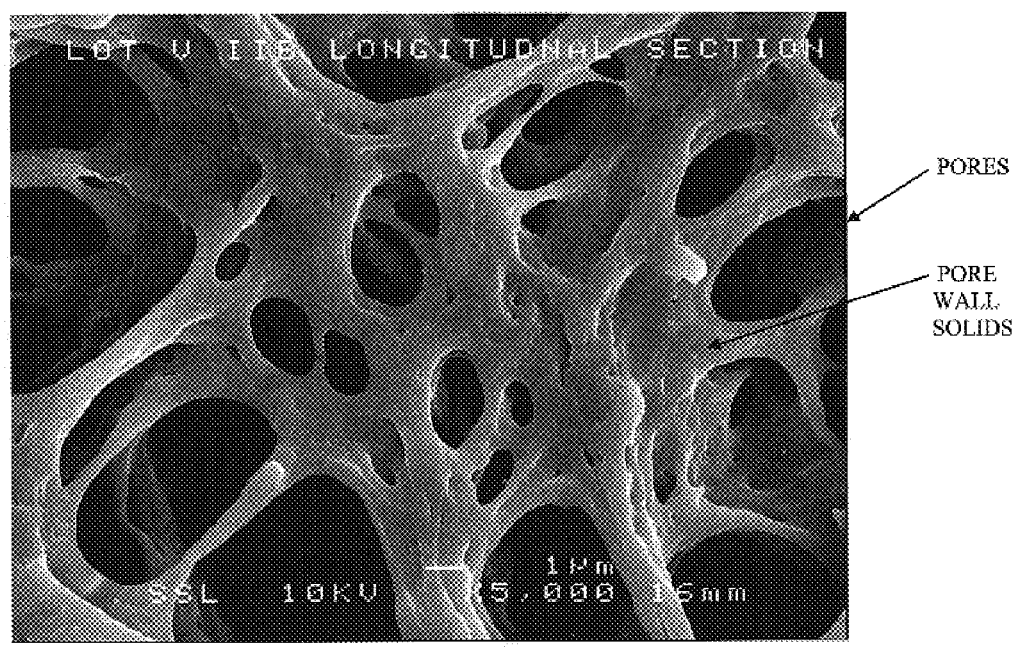
FIG. 6 shows a transverse view of the inner lumen wall of the fiber at a magnification of 5,000×.
Figure 7:
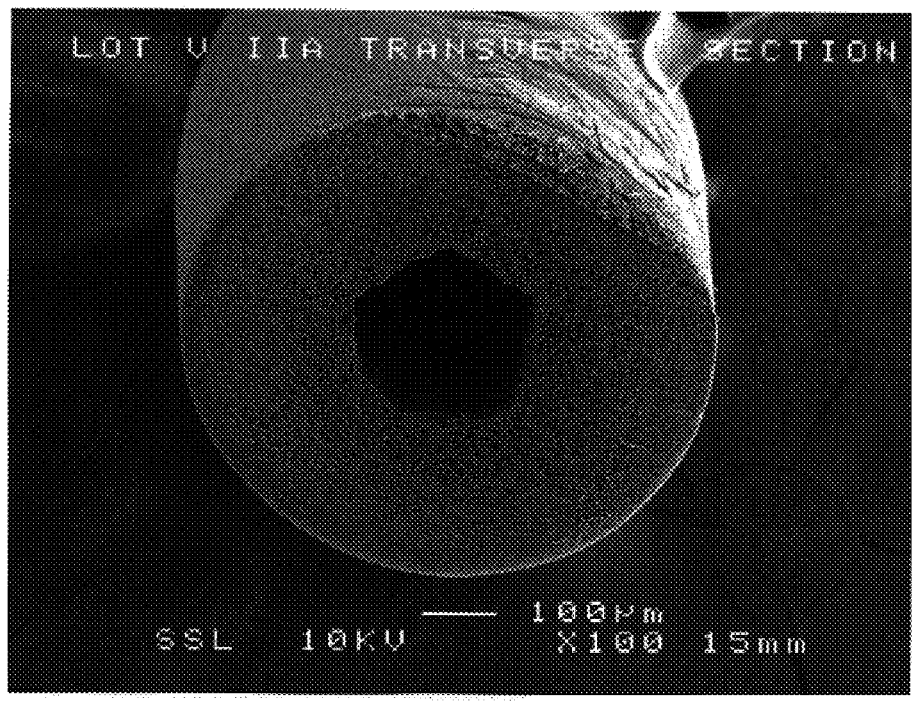
FIG. 7 is a SEM cross-section of a typical fiber at 100× magnification showing the asymmetrical wall structure.

As illustrated in FIGS. 1–7, the features of the fiber wall of the membrane of the invention include a pore and void structure defined within frames or solid walls which form boundaries of the pores. The pores are voids of variable definitive sizes which permit passage of fluid through the fiber wall to the lumen and which pores obstruct the passage of components larger than the pore diameter. As illustrated particularly in FIG. 3, the pores are irregular-shaped voids bounded by solid frames to form irregular tortuous paths for irregular and regular-shaped solutes. The wall structure of the fiber from the outer surface to the lumen is a continuum with non-linear pore and void distribution. The resulting structure is a continuous change in mass density between the outer surface of the fiber and the inner lumen surface and whereby the pore size gradually changes between the fiber wall surfaces. The fiber wall illustrated is substantially without macrovoids. The fiber wall structure of the elongated microporous fibers is asymmetrical between the inner wall surface extending along the interior fiber lumen and the outer fiber wall surface exposed to blood in the vessel in which the filter device is implanted. The fiber wall at or adjacent to the outer wall surface has a higher mass density than the mass density adjacent to or at the inner wall surface. The mass density is a function of the average nominal pore size. Such asymmetric fiber wall morphology is illustrated in FIG. 7 showing a scanning electron microscopy (SEM) image of a cross-section of the fiber at 100× magnification. It will be observed that the structure of the fiber from the outer surface to the lumen is substantially a continuous change in mass density whereby the pore size gradually changes between these fiber wall surfaces. It is convenient to describe these changes in mass density as sections of the wall area having an average nominal pore size, porosity and wall mass in terms of zones having macro-functions. The different mass density sections or zones of the wall area have an average nominal pore size or average pore diameter, each zone having a different average nominal pore size. The walls may be characterized by two or more zones, for example 2, 3, or 4 or more mass density zones.

Figure 1:
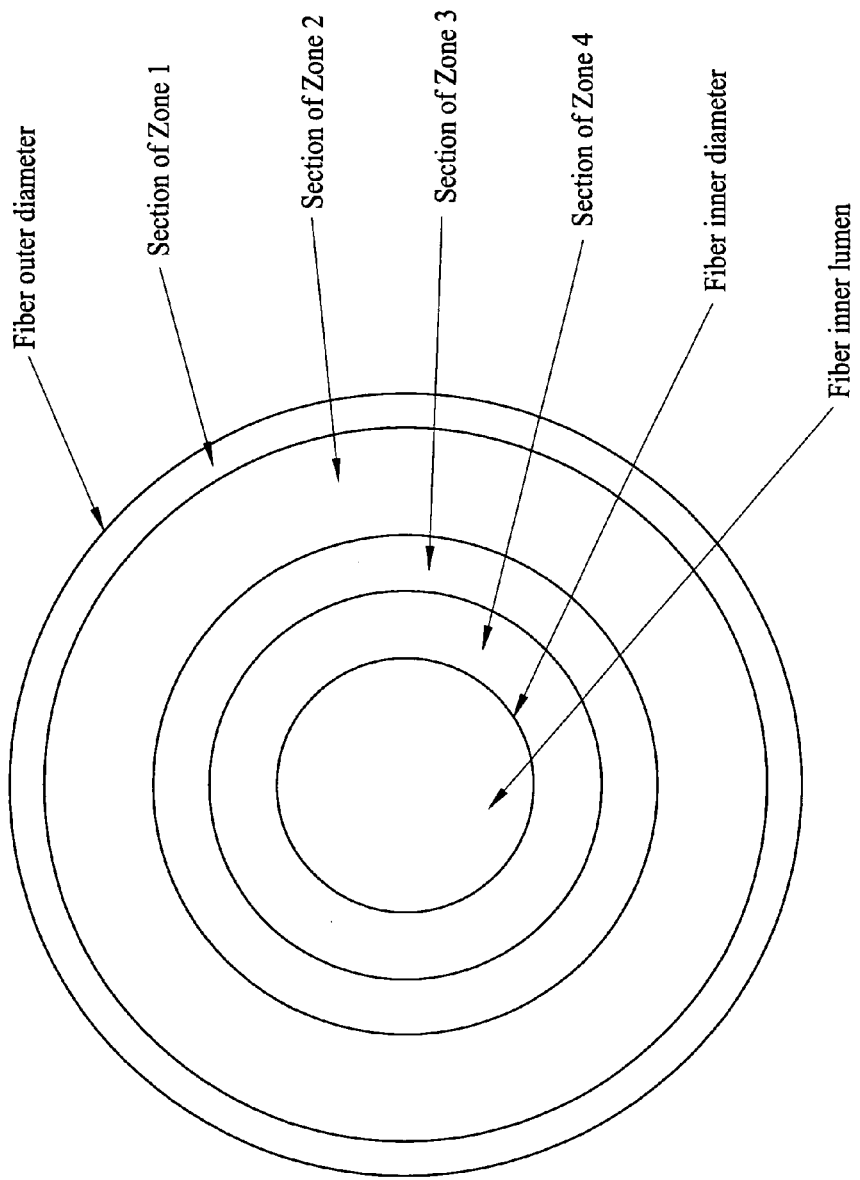
FIG. 1 is a schematic end view of a hollow fiber illustrating the membrane morphology structure having four zones.

By way of example, FIG. 1 schematically illustrates a cross-section of a typical fiber wall having four zone sections, each zone characterized by a different mass pore density based on the average nominal pore size in the respective zones. The section of Zone 1 is adjacent to the fiber outer surface or outer diameter. Zone 1 forms the fiber interface with the permeate blood flow and, although being the thinnest zone, contains the highest density of operationally controlling pores for determining the fiber membrane performance and filtration characteristics, including the composition and components of separated plasma, and controls fiber membrane performance. Thus, Zone 1 has the principal effect in the filtration process for controlling the trans-membrane flux (TMF) which is dependent on pore size, porosity and virtual membrane thickness. Nominal average pore diameters in Zone 1 are between about 0.3 μm and about 1 μm, and preferably range from about 0.4 μm to about 0.8 μm. A preferred filtration sizing has a cutoff of about 0.6 μm to about 0.8 μm.

Zones 2 and 3 are designed to decrease the flow path tortuosity and maintain the structural integrity required of the fiber exposed to physical conditions within the body. Pore size distribution in these zones may range gradually from about 0.8 μm to about 1.2 μm and from about 1.2 μm to about 2.5 μm, respectively. The section of Zone 2, while having some flux-controlling pores, is principally a structural member for providing strength to the fiber as well as acting as a conduit for exudate flow to the section of Zone 3. The latter is principally a structural member with expanded pores for reducing the hydraulic resistance and providing a fluid conduit to the lumen of the fiber, and thus, in the example, as shown, has little filtration function. Zone 4, representing the largest area having relatively large voids and pore diameters with little solid structure, has the primary function of a major reduction of hydraulic resistance through the membrane and defines the fiber inner lumen surface. Nominal average pore diameters in this lowest mass density zone are between about 1 μm and about 60 μm, and preferably between about 2 μm and about 6 μm. A typical fiber as shown has an OD of about 730±90 μm, an ID of about 230±70 μm and a wall thickness of about 245±75 μm. The pore sizes and zone dimensions given above are by way of example only.

Figure 2:
FIG. 2 is a scanning electron microscopy (SEM) image of a cross-section of a portion of the fiber of the invention at 400× magnification showing four zones of the asymmetrical wall structure between the inner and outer fiber wall surfaces.

FIG. 2 illustrates a cross-section of the fiber wall showing the structure of Zones 1–4 at 400× magnification. The fiber wall morphology demonstrates the continuum of expanding porosity and open spaces from the virtual control pore size of Zone 1 adjacent to the outer fiber diameter to the very open and low-flow resistant structure in Zone 4 adjacent to the inner lumen wall.

Figure 3:
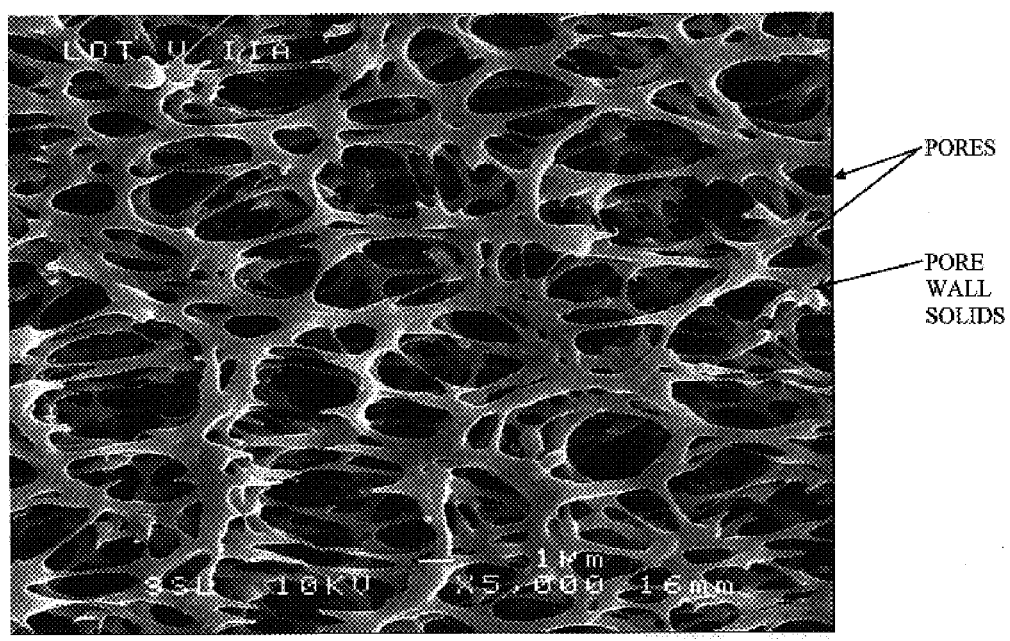
FIG. 3 shows a portion of a cross-section of a portion of the fiber at a magnification of 5,000×.

FIG. 3, a cross-section of Zone 1 at a magnification of 5,000×, shows pores and their boundary solid wall frames and the high uniformity of pore geometry and diverse irregular shapes of the individual pore dimensions. It is this high uniformity of pore size and high porosity as well as the thinness of Zone 1 which produces the high separation efficiency and high TMF of the membrane.

Figure 4:
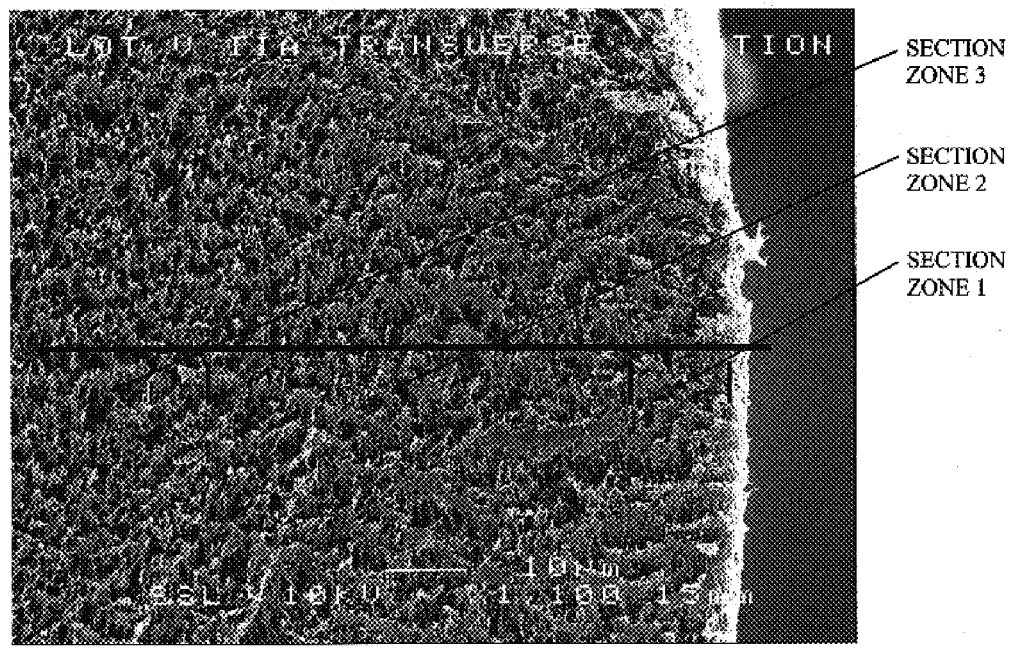
FIG. 4 is a SEM cross-section of Zones 1, 2 and 3 of the fiber shown in FIG. 2 at a magnification of 1,000×.

FIG. 4 shows a cross-section of Zones 1, 2 and 3 at a magnification of 1,000× to illustrate the transition of the high-density structure of Zone 1 in comparison to the more open densities of Zones 2 and 3, as well as the uniformity and continuity of fiber structure producing high tensile and elongation strength.

FIG. 5, also at a magnification of 1,000×, shows the structure of Zones 3 and 4 to illustrate the rapidly expanding open spaces and fluid communication channels which produce the lowered hydraulic resistance to flow of the exudate and results in a very high TMF as a function of a very low TMP.

FIG. 6 is a 5,000× magnification of a transverse view of the inner lumen wall showing the highly open but contiguous nature of the structure at that site, facilitating fluid communication of the exudate from the flow through fiber to the fiber lumen.

The driving force for convective transport of the plasma and solutes across the membrane is the transmembrane flux (TMF) equal to $P_f \times TMP$ (and linear below the critical flow limit) where $P_f$ is the hydraulic permeability of the membrane, and:

$$P_f = (n \pi r_p^4)/(\tau \mu \Delta x)$$

where:
(n)=Porosity (number of pores/unit area)
(π)=3.14159
($r_p$)=Pore radius (pore size)

(τ)=Tortuosity of flow path
(μ)=Viscosity of solution
(Δx)=Membrane thickness

The largest leverage to obtaining optimum TMF is the radius of the pores because it is raised to the fourth power, and thus the access fluid flow rate is increased exponentially. The next largest lever is the porosity or number of such pores/unit area and the effect of the pore radius which is multiplied by the porosity. Functional optimization for this application therefore also relies on achieving a tight standard deviation of pore radius in the effective zone of filtration as well as a high density of such pores in the primary filtration zone of the membrane. The relationship is also affected by temperature to the extent that temperature changes the value of the parameters including the viscosity of the solution.

The membranes described herein may be prepared using any suitable polymer which will result in a hollow fiber membrane which meets the required biocompatibility requirements and properties. Such membrane materials and surfaces must be highly biocompatible and resist clotting, protein adhesion and detrimental interaction with immune system components. The structural strength of the hollow fiber membranes must be high enough to safely withstand implantation as well as the hydraulic and physical perturbations existing in the vena cava environment. Thus, the functional convection extraction efficiency of such hollow fibers must be suitable to meet clinical treatment requirements in the smallest possible size in order to fit within the vena cava without stress. The membranes also must be designed with a morphology capable of separating plasma from whole blood by filtering from the outside to the inside (lumen) of the fiber. A number of potentially suitable polymer fiber membrane materials include polyurethane, polypropylene, polysulfone, polyethersulfone, polycarbonate, nylon, polyimide and other synthetic resins known to those skilled in the art. A preferred polymer is polysulfone, and more preferably a polyethersulfone blended with polyethylene oxide and/or polyethylene glycol or a polysulfone modified with a polyethylene oxide-polyethylene glycol copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. The specific method used for producing the aforesaid polymers as well as the processes and parameters during the manufacture are known to those skilled in the art, for example, PCT Publication WO 90/04609.

An important characteristic of the fibers to be used in a filter device capable of being implanted in a patient's blood vessel and separating plasma from blood therein, is the ability to withstand the rigors and effects of implantation procedures, and to function efficiently and effectively in-vivo at the pressures and flows to which it is exposed. In addition to adequate tensile strength, relatively high elongation and breaking strength, as indicating the ability of the fiber to withstand the adverse conditions to which it is exposed, is of substantial importance. The fibers described herein are characterized by an average elongation breaking force strength of at least about 0.2 lbs. and preferably at least about 0.25 lbs., and an average elongation of at least about 45%, preferably above 60% and more preferably 65% or more. Such characteristics make the fibers especially suitable to meet in-vivo plasma filtration performance demands. By way of example, tests of a polyethersulfone/polyethylene oxide polymer blend hollow fiber having a nominal inner diameter of 230 μm and outer diameter of 730 μm were tested for tensile strength, percent elongation and breaking force according to ASTM D 3822-01 standard methods. The results are shown in the following table:

| Sample | Break Strength (lbs) | % Elongation | Tensile (psi) |
|---|---|---|---|
| 1 | 0.352 | 76.7% | 748 |
| 2 | 0.335 | 60.0% | 712 |
| 3 | 0.379 | 75.8% | 806 |
| 4 | 0.375 | 75.2% | 797 |
| 5 | 0.360 | 75.7% | 765 |
| 6 | 0.355 | 69.5% | 755 |
| 7 | 0.343 | 68.5% | 729 |
| 8 | 0.334 | 63.6% | 710 |
| 9 | 0.363 | 69.2% | 772 |
| 10 | 0.341 | 65.8% | 725 |
| 11 | 0.340 | 70.5% | 723 |
| 12 | 0.354 | 61.2% | 753 |
| 13 | 0.366 | 72.4% | 778 |
| 14 | 0.324 | 70.2% | 689 |
| 15 | 0.358 | 77.7% | 761 |
| 16 | 0.342 | 66.6% | 727 |
| 17 | 0.393 | 72.9% | 835 |
| 18 | 0.346 | 74.5% | 736 |
| 19 | 0.339 | 71.5% | 721 |
| 20 | 0.353 | 77.8% | 750 |
| AVG | 0.353 | 70.8% | 750 |

The fibers described herein may be used in plasma separation filter devices such as described in the aforesaid patents. The fibers are especially suitable for use in a plasmapheresis filter described in U.S. Pat. No. 6,899,692 and in therapeutic apheresis apparatus described in U.S. Pat. No. 6,849,183. The descriptions of the aforesaid patents are incorporated in their entirety herein.

Specifications and variation range of parameters for preferred hollow fiber membranes described herein for medical applications are as follows:

| PLASMAPHERESIS APPLICATIONS | | | | |
|---|---|---|---|---|
| | SPECIFICATIONS | | RANGE OF APPLICATION | |
| PARAMETER | FROM | TO | FROM | TO |
| Outer Diameter μm | 640 | 820 | 200 | 1000 |
| Inner Diameter μm | 160 | 300 | 50 | 700 |
| Wall Thickness μm | 170 | 320 | 50 | 600 |
| Zone 1 mean flow pore diameter μm | 0.15 | 0.95 | 0.10 | 1 |
| Zone 4 pores @ ID diameter μm | 5 | 40 | 1 | 60 |
| Tensile force @ Break Pounds/in$^2$ | 600 | 1200 | 500 | 1500 |
| % Elongation @ Break | >45 | 100 | 45 | 150 |
| Elongation Break Strength (lbs. @ break) | >0.3 | 1.0 | 0.15 | 1.0 |
| Fluid Flux (H$_2$0) ml/min/cm$^2$ @ 100 mmHg | >1.0 | 12 | 1.0 | 30 |
| TMF plasma ml/min/cm$^2$/100 mmHg | >0.25 | 3 | .5 | 9 |

ULTRAFILTRATION APPLICATIONS

| PARAMETER | SPECIFICATIONS FROM | SPECIFICATIONS TO | RANGE OF APPLICATION FROM | RANGE OF APPLICATION TO |
|---|---|---|---|---|
| Outer Diameter μm | 640 | 820 | 200 | 1000 |
| Inner Diameter μm | 160 | 300 | 50 | 700 |
| Wall Thickness μm | 170 | 320 | 50 | 600 |
| Zone 1 mean flow pore diameter μm | 0.003 | 0.005 | 0.003 | 0.006 |
| Zone 4 pores @ ID diameter μm | 5 | 40 | 1 | 60 |
| TMF $H_2O$ ml/min/cm$^2$/500 mmHg | 0.15 | 2 | 0.15 | 9 |
| Tensile force @ Break Pounds/in$^2$ | 600 | 1200 | 500 | 1500 |
| Elongation @ Break % | >45 | 100 | 45 | 150 |
| Elongation Break Strength (lbs. @ break) | >0.3 | 1.0 | 0.15 | 1.0 |

Examples of medical applications for which the hollow fiber membranes of the present invention may be used include the following: therapeutic apheresis applications including plasma exchange, cascade protein separation by filtration, cascade protein removal or modification by adsorption cartridge, cryogenic modification, or chemical adaptation as described in U.S. Pat. No. 6,849,183; fluid management application or congestive heart failure both acute and chronic; tissue engineering applications including online generation of media for bioreactor from xenogenic, allogenic, and autogenic sources as described in U.S. Pat. No. 6,607,501; continuous renal replacement therapy (CRRT) for both acute and chronic kidney failure; edema prevention therapies for MODS (multiple organ dysfunction syndrome) as described in U.S. Pat. No. 6,632,192; cytokine removal or modification in therapy for septic shock or SIRS (systemic inflammatory response syndrome); plasma extraction from peritoneal ascites; intermittent hemodialysis (IHD) or hemodiafiltration; and ARDS (acute respiratory distress syndrome) therapy by reduction of pulmonary edema and physiological pulmonary dead space.

What is claimed is:

1. An in-vivo plasmapheresis and/or in-vivo ultrafiltration membrane comprising:
a plurality of elongated hollow fibers, each fiber comprising an outer wall, a higher mass density outer wall zone and an outer wall surface for being exposed to whole blood, wherein said higher mass density outer wall zone has a pore size capable of separating plasma and plasma components from whole blood by passing plasma and plasma components therethrough, and one or more lower mass density inner wall zones, an inner wall and an interior lumen extending along the length thereof and defined by an inner wall surface, and characterized by having an average elongation breaking force strength of at least about 0.2 lbs. and an average elongation of at least about 45%, and wherein the fiber wall structure is a continuous change in mass density from said outer wall surface to said inner wall surface and comprises a continuum of voids bounded by solid frames and substantially without macrovoids.

2. A membrane of claim 1 wherein said fiber wall has two mass density zones.

3. A membrane of claim 1 wherein said fiber wall has three mass density zones.

4. A membrane of claim 1 wherein fiber wall has four or more mass density zones.

5. A membrane of claim 1, 2, 3 or 4 wherein each of said mass density zones is characterized by a different average nominal pore size.

6. A membrane of claim 5 wherein said lower mass density inner wall zone is characterized by a nominal average pore diameter of between about 1 μm and about 60 μm.

7. A membrane of claim 5 wherein said higher mass density zone is characterized by a nominal average pore diameter of between about 0.10 μm and about 1 μm.

8. A membrane of claim 6 wherein said higher mass density zone is characterized by a nominal average pore diameter of between about 0.10 μm and about 1 μm.

9. A membrane of claim 5 wherein said higher mass density zone is characterized by a nominal average pore diameter of between about 0.003 μm and about 0.006 μm.

10. A membrane of claim 1, 2, 3 or 4 comprising polysulfone.

11. A membrane of claim 1, 2, 3 or 4 comprising polyethersulfone.

12. A membrane of claim 11 wherein said polyethersulfone is blended with polyethylene oxide and/or polyethylene glycol.

13. A membrane of claim 10 wherein said polysulfone is modified with polyethylene oxide-polyethylene glycol copolymer.

14. An in-vivo plasmapheresis or in-vivo ultrafiltration membrane comprising a plurality of elongated hollow fibers, each fiber having an outer wall, an inner wall and an interior lumen extending along the length thereof and defined by an inner wall surface, the fiber wall characterized by a higher mass density adjacent to the outer wall and an outer wall surface for being exposed to whole blood and having a pore size capable of separating plasma and plasma components from whole blood by passing plasma and plasma components therethrough and a lower density adjacent to said inner wall, and wherein the fiber wall structure is a continuous change in mass density from said outer wall surface to said inner wall surface and comprises a continuum of voids bounded by solid frames and substantially without macrovoids, said fiber wall having an asymmetrical pore size and asymmetrical mass density between said inner wall surface and the outer wall surface, said fiber further characterized by having an average elongation breaking force strength of at least about 0.3 lbs. and an average elongation of at least about 45%.

15. A membrane of claim 14 wherein the higher mass density fiber wall is characterized by pores having a smaller average nominal pore size as compared to the average nominal pore size in the lower mass density fiber wall.

16. A membrane of claim 15 wherein said lower mass density is characterized by a nominal average pore diameter of between about 1 μm and about 60 μm.

17. A membrane of claim 15 or 16 wherein said higher mass density is characterized by a nominal average pore diameter of between about 0.10 μm and about 1 μm.

18. A membrane of claim 15 wherein said higher mass density is characterized by a nominal average pore diameter of between about 0.003 μm and about 0.006 μm.

19. A membrane of claim 18 wherein said lower mass density is characterized by a nominal average pore diameter of between about 1 μm and about 60 μm.

20. A membrane of claim 16 having a plasma transmembrane flux of between about 0.5 ml/min/cm$^2$ and about 9 ml/min/cm$^2$ @ 100 mm Hg.

21. A membrane of claim 1 or 14 wherein said higher mass density is characterized by a nominal average pore diameter of between about 0.15 μm and about 1 μm.

22. A membrane of claim 21 wherein said lower mass density is characterized by a nominal average pore diameter of between about 5 μm and about 40 μm.

23. A membrane of claim 22 having a fluid flux ($H_2O$) of between about 1 ml/min/cm² and about 12 ml/min/cm² @100 mm Hg.

24. A membrane of claim 1 or 14 wherein said higher mass density is characterized by a nominal average pore diameter of between about 0.003 μm and about 0.006 μm.

25. A membrane of claim 24 wherein said lower mass density is characterized by a nominal average pore diameter of between about 5 μm and about 40 μm.

26. A membrane of claim 25 having a trans-membrane flux ($H_2O$) of between about 0.15 ml/min/cm² and about 2 ml/min/cm² @500 mm Hg.

27. A membrane of claim 14 comprising a polyethersulfone.

28. A membrane of claim 27 wherein said polyethersulfone is blended with polyethylene oxide and/or polyethylene glycol.

29. A membrane of claim 14 comprising a polysulfone.

30. A membrane of claim 14 comprising polysulfone modified with polyethyleneoxide-polyethylene glycol copolymer.

* * * * *